United States Patent
Wasserman et al.

(10) Patent No.: US 11,291,837 B2
(45) Date of Patent: Apr. 5, 2022

(54) UPLOADING DATA FROM AN ISOLATED SYSTEM WITHOUT COMPROMISING ISOLATION

(71) Applicant: Novocure GmbH, Root (CH)

(72) Inventors: Yoram Wasserman, Haifa (IL); Golan Bar-Tal, Zichron Ya'akov (IL); Michael Varshaver, Durham, NH (US); Shimon Elkabetz, Tiberias (IL)

(73) Assignee: Novocure GmbH, Root (CH)

( * ) Notice: Subject to any disclaimer, the term of this patent is extended or adjusted under 35 U.S.C. 154(b) by 69 days.

(21) Appl. No.: 16/846,672

(22) Filed: Apr. 13, 2020

(65) Prior Publication Data

US 2020/0330755 A1 Oct. 22, 2020

Related U.S. Application Data

(60) Provisional application No. 62/835,147, filed on Apr. 17, 2019.

(51) Int. Cl.
*A61N 1/36* (2006.01)
*A61N 1/02* (2006.01)
*A61B 5/01* (2006.01)

(52) U.S. Cl.
CPC ......... *A61N 1/36002* (2017.08); *A61N 1/025* (2013.01); *A61N 1/36031* (2017.08); *A61B 5/01* (2013.01)

(58) Field of Classification Search
CPC ............ A61N 1/36002; A61N 1/36031; A61N 1/025; A61B 5/01
See application file for complete search history.

(56) References Cited

U.S. PATENT DOCUMENTS 5,233,987 A   8/1993  Fabian et al.
6,868,289 B2  3/2005  Palti
(Continued)

FOREIGN PATENT DOCUMENTS

EP       0801959 A2    10/1997
WO    2011047211 A1     4/2011
(Continued)

OTHER PUBLICATIONS

Partial International Search Report and Written Opinion issued in application No. PCT/IB2020/053472 dated Jul. 7, 2020.
(Continued)

*Primary Examiner* — Ankit D Tejani
*Assistant Examiner* — Joshua Brendon Solomon
(74) *Attorney, Agent, or Firm* — Potomac Law Group, PLLC (57) ABSTRACT

A data transfer apparatus ("DTA") connects to the field generator in a TTFields therapy system using the same connector on the field generator that is used to connect a transducer interface to the field generator. The field generator automatically determines whether the transducer interface or the DTA is connected to it. When the transducer interface is connected to the field generator, the field generator operates to deliver TTFields therapy to a patient. On the other hand, when the DTA is connected to the field generator, the field generator transfers patient-treatment data to the DTA, and the DTA accepts the data from the field generator. After the field generator and the DTA have been disconnected, the DTA transmits the data to a remote server, e.g., via the Internet or via cellular data transmission.

11 Claims, 11 Drawing Sheets

(56) References Cited

U.S. PATENT DOCUMENTS

| | | |
|---|---|---|
| 7,016,725 B2 | 3/2006 | Palti |
| 7,089,054 B2 | 8/2006 | Palti |
| 7,136,699 B2 | 11/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 2006/0167499 A1 | 7/2006 | Palti |
| 2007/0191912 A1 | 8/2007 | Fischer et al. |
| 2007/0225766 A1 | 9/2007 | Palti |
| 2007/0239213 A1 | 10/2007 | Palti |
| 2009/0076366 A1 | 3/2009 | Palti |
| 2009/0182394 A1 | 7/2009 | Bachinski |
| 2012/0283726 A1 | 11/2012 | Palti |
| 2014/0330268 A1 | 11/2014 | Palti et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |

FOREIGN PATENT DOCUMENTS

| | | |
|---|---|---|
| WO | 2018033842 A1 | 2/2018 |
| WO | 2018156804 A1 | 8/2018 |

OTHER PUBLICATIONS

International Search Report and Written Opinion issued in application No. PCT/IB2020/053472 dated Aug. 28, 2020.

Extended European Search Report issued in application No. Ep 21193671 dated Jan. 26, 2022.

UPLOADING DATA FROM AN ISOLATED SYSTEM WITHOUT COMPROMISING ISOLATION

CROSS REFERENCE TO RELATED APPLICATIONS

This application claims the benefit of U.S. Provisional Application 62/835,147, filed Apr. 17, 2019, which is incorporated herein by reference in its entirety.

FIELD OF THE INVENTION

In general, this application is directed uploading data from an isolated medical device without compromising isolation of the medical device. More specifically, the application is directed to a data transfer apparatus ("DTA") for use with the medical device, which DTA facilitates remote monitoring of treatment using the medical device.

BACKGROUND

Figure 1:
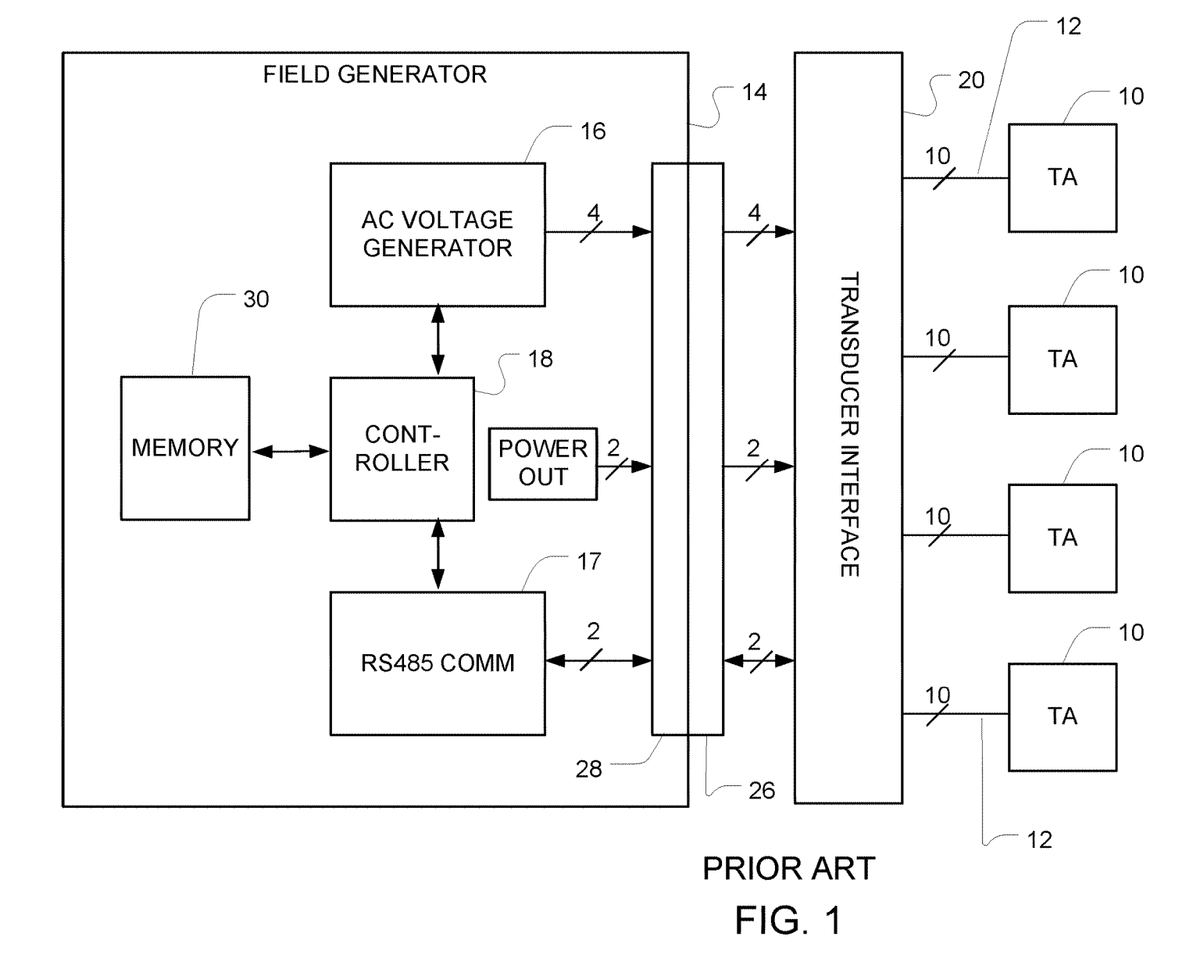
FIG. 1 is a schematic diagram illustrating a system for TTFields treatment therapy according to the prior art.

In general, TTFields (tumor-treating fields) therapy is a proven approach for treating tumors. In a prior art Optune® system for delivering TTFields as illustrated in FIG. 1, the TTFields are delivered to patients via four transducer arrays 10 placed on the patient's skin in close proximity to a tumor. The transducer arrays 10 are arranged in two pairs, and each transducer array 10 is connected via a multi-wire cable to a transducer interface 20, which, in turn, is connected to a field generator 14 via a connector. The field generator 14 (a) sends an AC current through one pair of arrays 10 during a first period of time; then (b) sends an AC current through the other pair of arrays 10 during a second period of time; then repeats steps (a) and (b) for the duration of the treatment.

The field generator 14 includes an AC voltage generator 16 and a controller 18. The amplitude of the alternating current that is delivered via the transducer arrays 10 is controlled by the controller 18 so that skin temperature (as measured on the skin below the transducer arrays) does not exceed a safety threshold of 41 degrees Celsius. The temperature measurements on the patient's skin are obtained using thermistors (not shown) placed beneath some of the disks (not shown) of the transducer arrays 10. In the existing Optune® system, each array 10 includes 8 thermistors, with one thermistor positioned beneath a respective disk in the array.

The temperature from all 32 thermistors (4 arrays×8 thermistors per array) is measured and analog-to-digitally converted into digital values for each thermistor. These measurements are then transmitted from the transducer interface 20 to the field generator 14. The controller 18 in the field generator 14 uses the temperature measurements to control the current to be delivered via each pair of arrays 10 in order to maintain temperatures below 41 degrees Celsius on the patient's skin.

In the existing Optune® system, there are four long 10-wire cables 12, each of which runs between a respective array 10 and the transducer interface 20, and one 8-wire spiral cord (not illustrated specifically) that runs between the transducer interface 20 and the connector 28 on the field generator 14. Each of the 10-wire cables 12 has 8 wires for carrying signals from the 8 thermistors, 1 wire for the common of all 8 thermistors, plus 1 wire for providing the TTFields signal (i.e., current) to the array 10. The 8-wire spiral cord has 1 wire for power to the transducer interface 20 (Vcc), supplied by a power source in the field generator; 1 wire for ground to the transducer interface 20; 2 wires for serial data communication (to send the temperature readings from the transducer interface 20 to the field generator 14); plus 4 wires for TTFields signals (i.e., one signal for each of the four arrays 10). The 8-wire spiral cord has a second connector 26 at its end, which interfaces with the first connector 28 on the field generator 14.

Furthermore, so that a care provider can monitor a patient's course of treatment, the field generator 14 includes one or more data storage registers (i.e., memory) 30, where patient-treatment data is stored. Information in the treatment data may include, for example, time and date of treatment sessions; current applied by each transducer array 10; temperatures measured by the thermistors; any anomalies; etc. Currently, the treatment data that has been stored in the field generator can only be accessed by having the patient bringing the Optune® system to a facility, where technical staff accesses and downloads the data via a dedicated service-port.

SUMMARY OF THE INVENTION

The disclosed apparatus facilitates the transfer of data from an Optune® system to a remote facility without requiring the patient to transport the Optune® system. Thus, the disclosed apparatus features a data transfer apparatus ("DTA") that connects to the field generator (where the patient-treatment data is stored) using the same single connector that was traditionally used to attach the transducer interface to the field generator. The field generator is configured to automatically determine whether the transducer interface or the DTA is connected to it. When the transducer interface is connected to the field generator, the field generator applies AC voltages to the transducer arrays (via the transducer interface) to deliver TTFields therapy to the patient. On the other hand, when the DTA is connected to the field generator, the field generator transfers the patient-treatment data to the DTA, and the DTA accepts the data from the field generator. Subsequently after the DTA has been disconnected from the field generator, the DTA transmits the data to a remote server, e.g., via the Internet (wirelessly or via wired connection) or via cellular data transmission.

Because the data is transmitted to the remote server, this arrangement eliminates the need for the patient to bring the Optune® system to a facility, which is a significant convenience for the patient. Furthermore, because the same single connector is used to attach the DTA or the transducer interface to the field generator, there is no risk of erroneously applying current from a DTA to the transducers (and hence to the patient). In other words, electrical isolation of the patient from signals other than those generated by the field generator is maintained. Further still, providing a DTA as a distinct device—in contrast to incorporating data transmission hardware into the field generator—avoids the need for data-transmission certification (e.g., by the Federal Communications Commission) in addition to medical-device certification (e.g., by the Food and Drug Administration).

One aspect of the invention is directed to a data transfer apparatus for use in association with a field generator of a TTFields (tumor-treating fields) therapy system. The field generator has a first connector that is used to output AC signals and convey serial data. The data transfer apparatus comprises a serial data transceiver; a memory; a modem; and a second connector configured to interface with the first connector. The data transfer apparatus also comprises a controller programmed to execute instructions that cause the data transfer apparatus to execute the following steps: (1) determining that the field generator has been connected to the data transfer apparatus; (2) after determining that the field generator has been connected to the data transfer apparatus, causing the serial data transceiver to accept serial data from the field generator and to store the accepted data in the memory, wherein the accepted data is data relating to treatment of a patient using TTFields; (3) after accepting the data from the field generator, determining whether the field generator has been disconnected from the data transfer apparatus; and (4) after determining that the field generator has been disconnected from the data transfer apparatus, retrieving data relating to treatment of a patient using TTFields from the memory and causing the modem to transmit the retrieved data to a remote server.

In some embodiments of the data transfer apparatus, the controller is programmed to cause the field generator to clear TTFields treatment-related data that has been stored in the field generator once all data relating to treatment of a patient using TTFields has been accepted.

In some embodiments of the data transfer apparatus, the modem is configured to transmit data via the Internet. In some embodiments of the data transfer apparatus, the modem is configured to transmit data via a cellular data network.

Some embodiments of the data transfer apparatus further comprise a switch that actuates upon physical connection of another device to the data transfer apparatus. In these embodiments, the controller is programmed to determine that the field generator has been connected to the data transfer apparatus by detecting a state of the switch. Optionally, in these embodiments, the controller is further programmed to determine that the field generator has been disconnected from the data transfer apparatus by detecting the state of the switch.

In some embodiments of the data transfer apparatus, the connection between the field generator and the data transfer apparatus interface is implemented by mating the second connector directly to the first connector.

In some embodiments of the data transfer apparatus, the connection between the field generator and the data transfer apparatus interface is implemented by connecting a cable between the second connector and the first connector.

Another aspect of the invention is directed to a TTFields (tumor-treating fields) therapy field generator. The field generator comprises an AC voltage generator; a serial data transceiver; a memory; and a single first connector having 1) a first plurality of pins for outputting an AC voltage generated by the AC voltage generator, and 2) a second plurality of pins for conveying serial data to and from the serial data transceiver. The field generator also comprises a controller programmed to execute instructions that cause the field generator to perform the following steps: (1) determining if a transducer interface has been connected to the first connector; (2) after determining that the transducer interface has been connected to the first connector, activating the AC voltage generator so that an AC voltage appears across the first plurality of pins of the first connector, and storing data relating to TTFields treatment in the memory; (3) determining if a data transfer apparatus has been connected to the first connector; and (4) after determining that a data transfer apparatus has been connected to the first connector, retrieving the data related to TTFields treatment from the memory and routing the retrieved data to the serial data transceiver so that the serial data transceiver outputs the data relating to TTFields treatment via the second plurality of pins of the single first connector.

In some embodiments of the field generator, the controller is programmed to determine that a transducer interface has been connected to the first connector by examining data received via the serial data transceiver.

In some embodiments of the field generator, the controller is programmed to determine that a data transfer apparatus has been connected to the first connector by examining data received via the serial data transceiver.

In some embodiments of the field generator, the controller is programmed to clear data relating to TTFields treatment from the memory after the data relating to TTFields treatment has been output by the serial data transceiver.

In some embodiments of the field generator, the data relating to TTFields therapy stored in the memory includes one or more of time and date of treatment sessions, current applied by each transducer array in a set of transducer arrays that has been connected to the first connector, measured temperature values, and operational anomalies.

Another aspect of the invention is directed to a TTFields (tumor-treating fields) therapy system with enhanced diagnostics. The system comprises a field generator; and a data transfer apparatus. The field generator includes an AC voltage generator, a first serial data transceiver, a first memory, a single first connector having 1) a first plurality of pins for outputting an AC voltage generated by the AC voltage generator, and 2) a second plurality of pins for conveying serial data to and from the first serial data transceiver, and a first controller. The first controller is programmed to execute instructions that cause the field generator to perform the following steps: (1) determining if a transducer interface has been connected to the first connector, (2) after determining that the transducer interface has been connected to the first connector, activating the AC voltage generator so that an AC voltage appears across the first plurality of pins of the first connector, and storing data relating to TTFields treatment in the first memory, (3) determining if a data transfer apparatus has been connected to the first connector, and (4) after determining that a data transfer apparatus has been connected to the first connector, retrieving the data related to TTFields treatment from the first memory and routing the retrieved data to the first serial data transceiver so that the first serial data transceiver outputs the data relating to TTFields treatment via the second plurality of pins of the single first connector. The data transfer apparatus includes a second serial data transceiver, a second memory, a modem, a second connector configured to interface with the first connector, and a second controller. The second controller is programmed to execute instructions that cause the data transfer apparatus to execute the following steps: (1) determining that the field generator has been connected to the data transfer apparatus, (2) after determining that the field generator has been connected to the data transfer apparatus, causing the second serial data transceiver to accept serial data from the field generator and to store the accepted data in the second memory, wherein the accepted data is data relating to treatment of a patient using TTFields, (3) after accepting the data from the field generator, determining whether the field generator has been disconnected from the data transfer apparatus, and (4) after determining that the field generator has been disconnected from the data transfer apparatus, retrieving data relating to treatment of a patient using TTFields from the second memory and causing the modem to transmit the retrieved data to a remote server.

In some embodiments of the system, the first controller is programmed to (a) determine that the transducer interface has been connected to the first connector by examining data received via the first serial data transceiver, and (b) determine that the data transfer apparatus has been connected to the first connector by examining data received via the first serial data transceiver.

In some embodiments of the system, the first controller is programmed to clear data relating to TTFields treatment from the first memory after the data relating to TTFields treatment has been output by the first serial data transceiver.

In some embodiments of the system, the data relating to TTFields therapy stored in the first memory includes one or more of time and date of treatment sessions, current applied by each transducer array in a set of transducer arrays that has been connected to the first connector, measured temperature values, and operational anomalies.

In some embodiments of the system, the connection between the field generator and the data transfer apparatus interface is implemented by mating the second connector directly to the first connector. In some embodiments of the system, the connection between the field generator and the data transfer apparatus interface is implemented by connecting a cable between the second connector and the first connector.

DESCRIPTION OF THE PREFERRED EMBODIMENTS

FIGS. 2A, 2B, 3, 4A, 4B, and 5A-5E illustrate components for use in association with TTFields treatment therapy in accordance with the invention. In general, the components include a field generator 40 four transducer arrays 10 and a transducer interface 20, and a data transfer apparatus (DTA) 42.

Figure 2A:
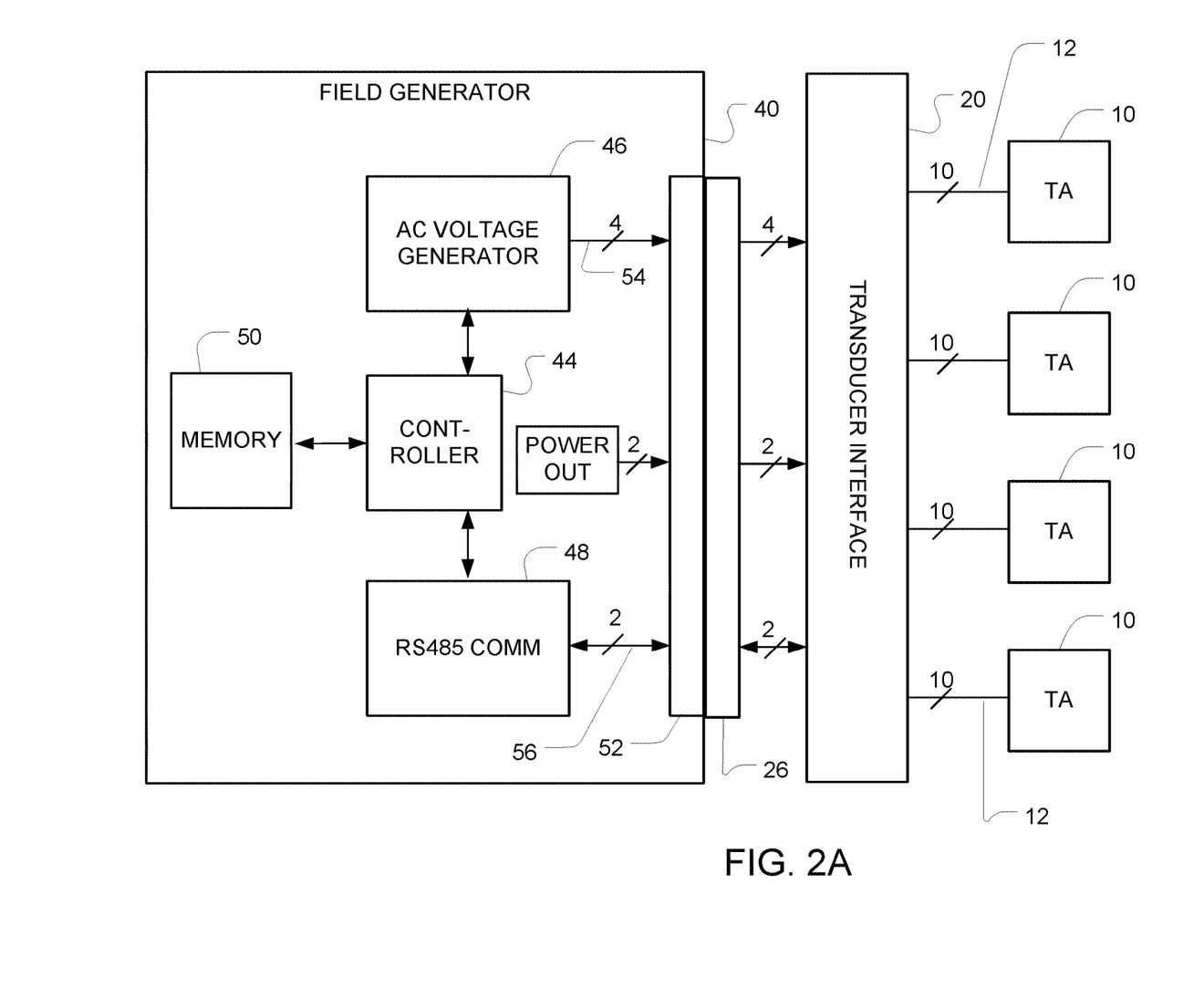
FIG. 2A is a schematic diagram illustrating a set of transducer arrays connected to a field generator.
Figure 2B:
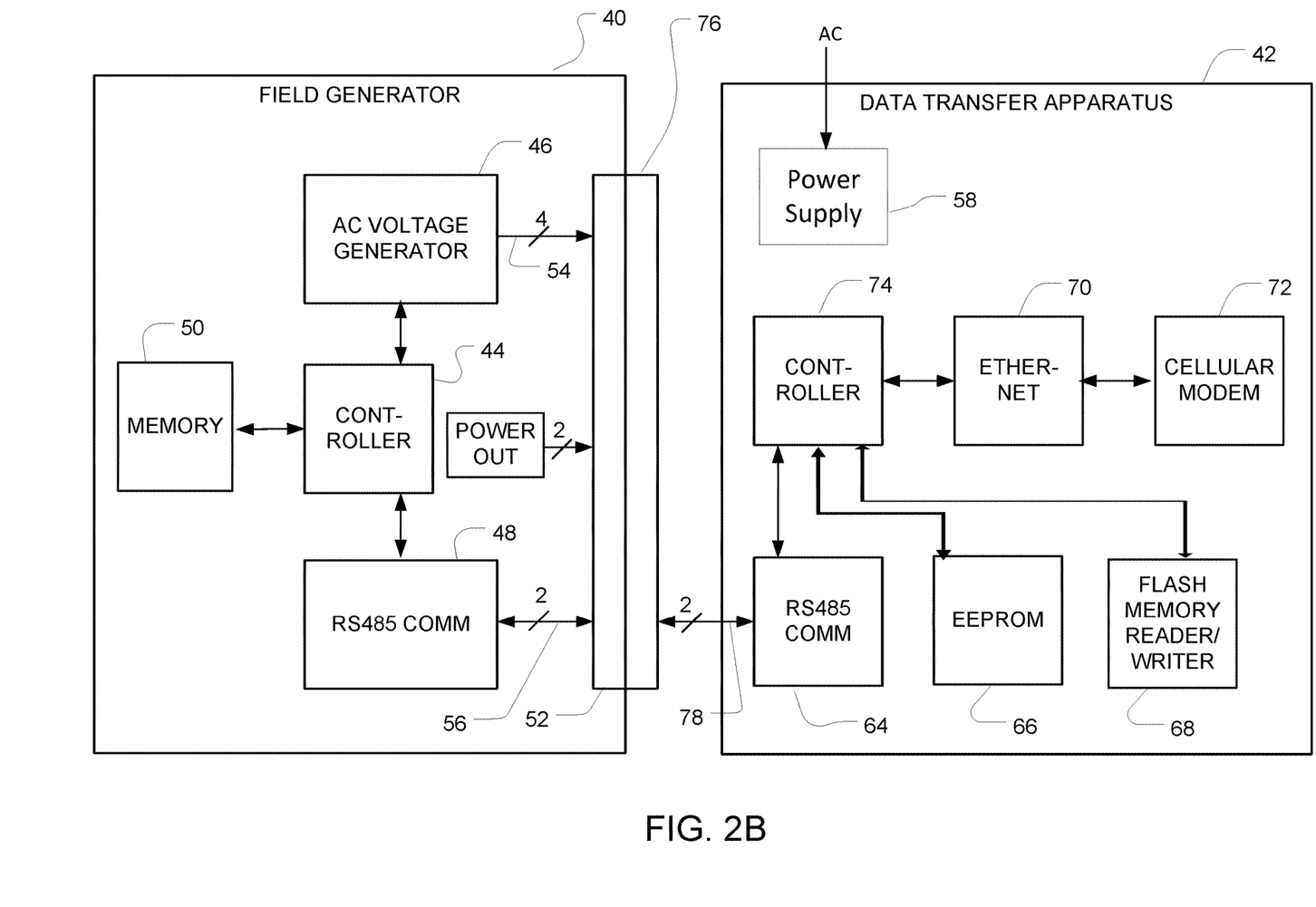
FIG. 2B is a schematic diagram illustrating a DTA connected to a field generator.

As illustrated in FIGS. 2A and 2B, the field generator 40 includes a controller 44; an AC voltage generator 46 that is similar to the AC voltage generator 16 in FIG. 1; a serial data transceiver 48, e.g., an RS485 communications circuit is similar to the RS-485 communication circuit 17 in FIG. 1; memory 50; and a field generator connector 52. The controller 44 is programmed to perform most of the functions of the controller 18 of FIG. 1, but the controller 44 also performs several additional functions. In particular, the controller 44 is programmed to determine whether a transducer interface 20 or a DTA 42 is connected to the field generator connector 52. If a transducer interface 20 is connected to the field generator connector 52 as illustrated in FIG. 2A, then the controller 44 operates similarly to the controller 18 and causes TTFields therapy to be delivered to a patient by activating the AC voltage generator 46. On the other hand, if a DTA 42 is connected to the field generator connector 52 as illustrated in FIG. 2B, then the controller 44 controls the transfer of TTFields therapy-related data from the field generator 40 to the DTA 42, so that the DTA can subsequently transmit the TTFields therapy-related data to a remote server, e.g., at a data center.

The field generator connector 52 (also referred to herein as the "first connector") is configured to interface with a transducer interface 20 via the second connector 26 of the transducer interface 20 as illustrated in FIG. 2A, so that AC current generated by the field generator 40 can be applied to a patient for TTFields therapy. Four wires 54 extend from the voltage generator 46 and carry current (the TTFields signals) that will be provided to each of the four transducer arrays 10, and 2 wires 56 extend from the serial data transceiver 48 for serial data communication of temperature readings from the transducer interface 20. These wires 54 and 56 terminate in respective electrical connection pins (not illustrated) in the field generator connector 52. (The term "pins" as used herein could refer to male or female connection terminals.)

As illustrated in FIG. 2B, the DTA 42 includes an AC-powered power supply 58, a serial data transceiver 64, e.g., an RS485 communications circuit, and memory, e.g., EEPROM 66, which can store data related to treatment of the patient using TTFields therapy that has been received from the field generator 40 (as described further below) as well as system settings. The DTA 42 may also include flash memory reader/writer 68, which can be used to store LOG data backup to, e.g., an SD card. The DTA 42 also includes at least one communications modem, e.g., Internet modem 70 and/or cellular data modem 72. Further still, the DTA 42 includes a controller 74, which is programmed to control operation of the DTA 42 as described further below.

The DTA 42 has a DTA connector 76 (also referred to herein as a second connector), which is configured to interface with the field generator connector 52. Two wires 78 extend from the serial data transceiver 64, and they provide a serial data communication pathway for the DTA 42 to accept from the field generator 40 data related to treatment of the patient using TTFields therapy. These wires 78 terminate in electrical connection pins (not illustrated) in the DTA connector 76 which mate with the corresponding pins of the field generator connector 52.

Figure 3:
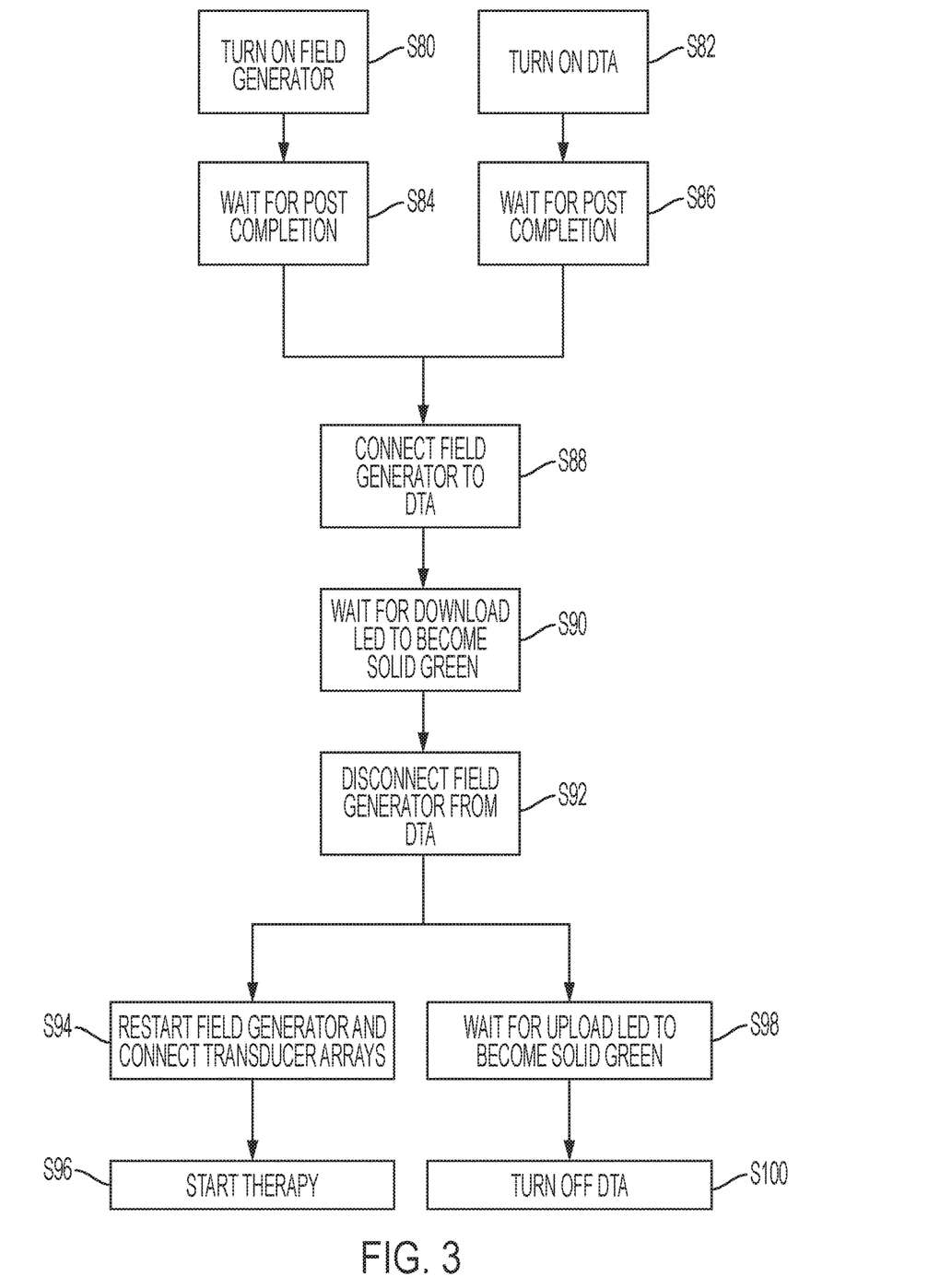
FIG. 3 is a flowchart illustrating steps a patient takes when using a system for uploading TTField treatment therapy-related data.

One example of using the hardware depicted in FIG. 2A/2B to upload TTFields treatment therapy-related data is illustrated in FIG. 3. A data-transfer session starts with the field generator 40 being turned on (S80) and the DTA 42 being turned on (S82). The field generator 40 and the DTA 42 each perform a power-on self-test S84, S86, and when the self-tests are completed an indicator (e.g., an LED) will illuminate on each of the units. At that point, the field generator 40 can be connected to the DTA 42 (S88) by connecting the field generator connector 52 to the DTA connector 76. Data stored in the field generator 40 that is related to TTFields treatment therapy will then be 1) transferred to the DTA 42, and 2) cleared from the field generator 40, after which another indicator (e.g., an LED) on each device will be illuminated (S90). The field generator 40 may then be disconnected from the DTA 42 (S92).

Once the field generator 40 has been disconnected from the DTA 42, the field generator 40 may be restarted and the transducer arrays connected to it (S94) by connecting the second connector 26 of the transducer interface 20 to the field generator connector 52, as illustrated in FIG. 2A. TTFields therapy may then be begun (S96).

Additionally, once the field generator 40 has been disconnected from the DTA 42—and only after the field generator 40 has been disconnected from the DTA 42—the DTA 42 will begin to transmit the TTFields therapy-related data that it has received from the field generator 40 to a remote server. By not transmitting the TTFields-related data until after the field generator 40 has been disconnected from the DTA 42, isolation of the field generator 40 and hence the overall TTFields therapy treatment system—can be maintained. Thus, this arrangement protects the patient. Additionally, it avoids having to certify the TTFields treatment system as a data communications device in addition to being certified as a medical device.

Once the DTA 42 has transmitted all the received TTFields treatment-related data to the remote server, an indicator (e.g., an LED) illuminates (S98), and the DTA 42 may be turned off (S100).

Some examples of suitable operational logic for the field generator 40 and DTA 42 are illustrated in FIGS. 4A, 4B, and 5A-5E. (Note that where this description refers to the field generator 40 or DTA 42 performing a particular step, it should be understood as meaning that respective controller 44 or 74 is programmed to perform the particular step.)

Figure 4A:
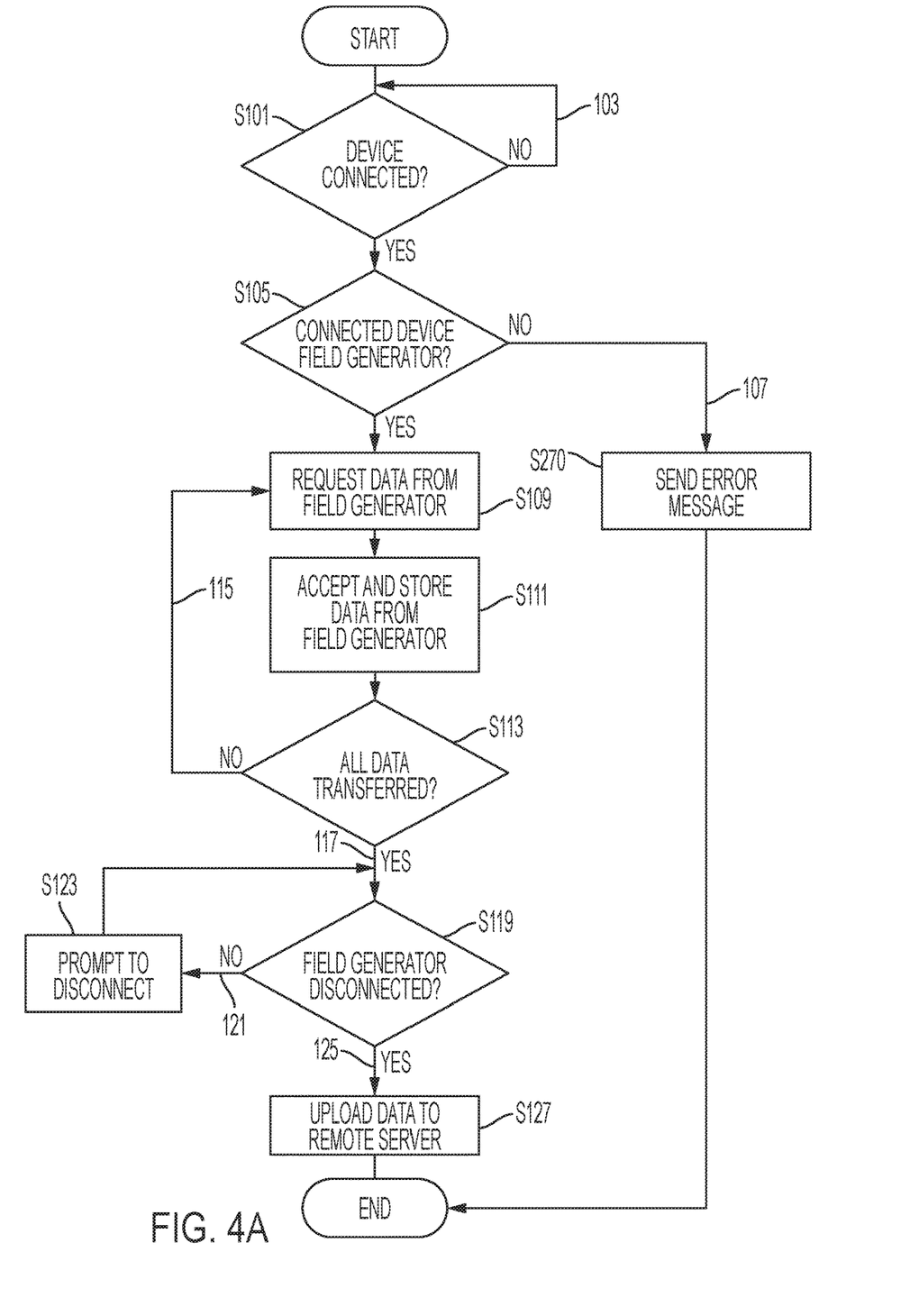
FIGS. 4A and 4B are high-level flowcharts illustrating the overall operation of a DTA and a field generator, respectively.

At a general level, operational logic of the DTA 42 (shown in FIG. 2B) is illustrated in FIG. 4A. The process begins (S101) with the DTA 42 determining whether a device is connected to it via the DTA connector 76. If no device is connected to the DTA 42 (result path 103), the process returns to the top and the DTA 42 continues to monitor for a device being connected to it.

On the other hand, if a device is connected to the DTA 42, flow proceeds to step S105 where the DTA 42 determines whether the connected device is the field generator 40. If the connected device is not the field generator 40 (result path 107), an error message is sent (S270) and the process terminates. Otherwise, the DTA 42 requests (S109) TTFields therapy-related data from the field generator 40, then accepts and stores the data (S111) in its onboard memory 66. Each time the DTA 42 receives data from the field generator 40, the DTA 42 queries (S113) as to whether there is any more data to be transferred. So long as data remains in the field generator 40 to be transferred to the DTA 42 (result path 115), the DTA 42 will continue to accept and store data from the field generator 40.

Once all data has been transferred from the field generator 40 to the DTA 42 (result path 117), the DTA 42 determines whether the field generator 40 has been disconnected from the DTA 42 (S119). If the field generator 40 has not been disconnected from the DTA 42 (result path 121), it prompts the user to disconnect the field generator (S123). On the other hand, once the field generator 40 has been disconnected from the DTA 42 (result path 125), the DTA 42 uploads the data it has received from the field generator 40 to a remote server (S127).

Figure 4B:
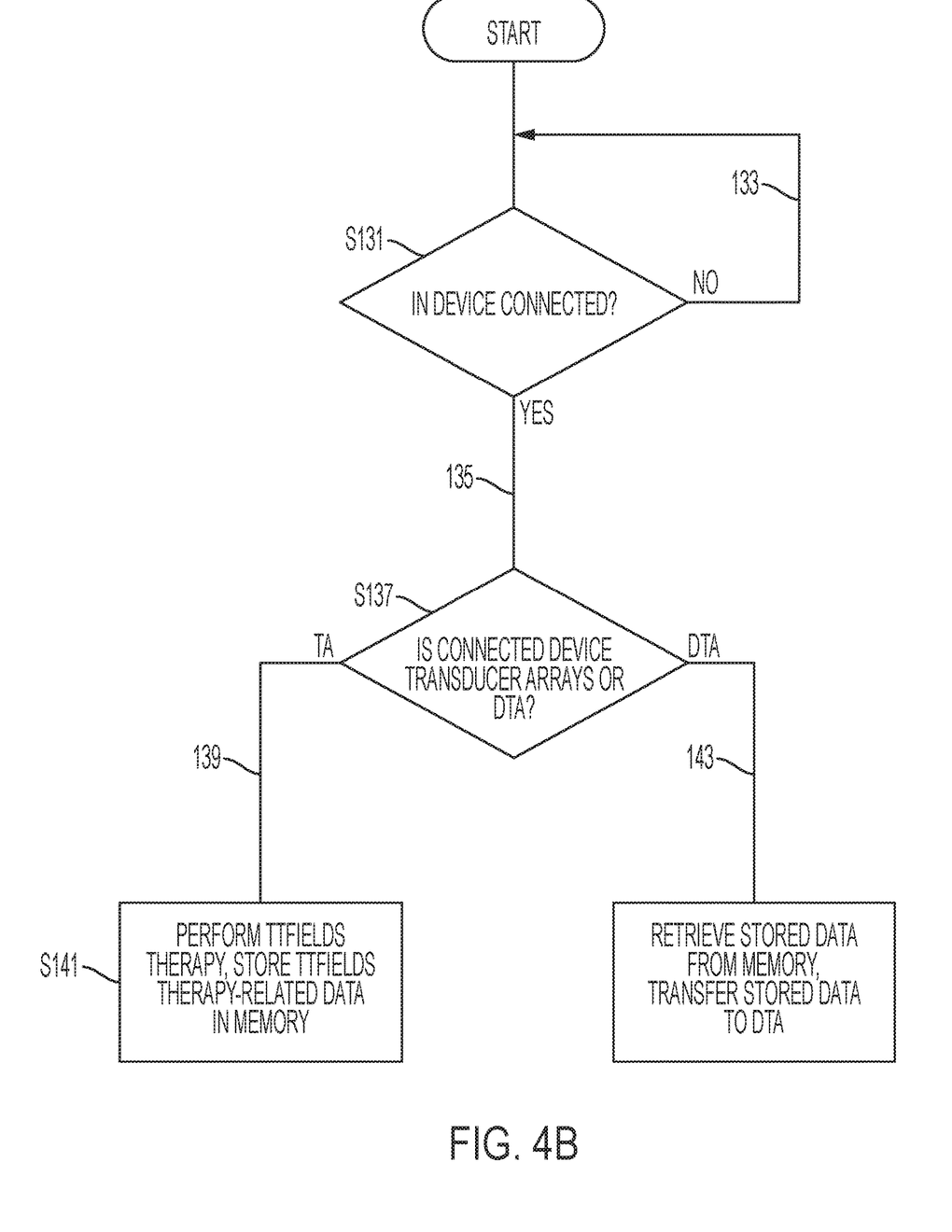

Operational logic for the field generator 40 (shown in FIGS. 2A and 2B) is shown at a general level in FIG. 4B. The process begins (S131) with the field generator 40 determining whether a device is connected to it via the field generator connector 52. Once it is turned on, the field generator begins to send communication requests once a second via the field generator connector 52. Therefore, if there is no device connected to the field generator 40 (result path 133), there will be no response to the field generator's communications request, and the field generator 40 will continue waiting until a device is, in fact, connected to it. On the other hand, if a device is connected to the field generator 40 (result path 135), the field generator 40 determines in step S137 whether the connected device is a set of transducer arrays 10 (connected to the field generator 40 via the transducer interface 20, as depicted in FIG. 2A) or a DTA 42 (as depicted in FIG. 2B). This may be accomplished, for example, by examining device-identifying data received from whichever device is connected to the field generator.

If the connected device is a set of transducer arrays 10 (result path 139), the field generator 40 provides AC voltage to the transducer arrays 10 to provide TTFields therapy to the patient (S141), storing TTFields therapy-related data in its memory 50 as it does so. On the other hand, if the connected device is a DTA 42 (result path 143), the field generator 40 retrieves stored TTFields therapy-related data from its memory 50 and transfers the retrieved data to the DTA 42 (S145), for subsequent uploading by the DTA 42 to the remote server.

FIGS. 5A-5E depict in greater detail one example of how data can flow between the field generator 40 and the DTA 42 when the field generator 40 is connected to the DTA 42, and between the DTA 42 and the remote server when the field generator 40 is not connected to the DTA 42. Note however, that a wide variety of alternative approaches may be used. Operation begins once the power-on self-tests have been completed for each of the field generator 40 and the DTA 42 (S84, S86, respectively). Once the power-on self-test in the field generator 40 is completed, the field generator 40 begins to "listen" for incoming requests to communicate (S108).

Meanwhile, once the power-on self-test in the DTA 42 is completed, the DTA checks (S110) to determine whether there is enough memory available in the DTA 42 (e.g., in EEPROM 66 and/or in an SD card inserted into the flash memory reader/writer 68) to receive and store a complete set of TTFields therapy-related data from the field generator 40. If enough memory is not available in the DTA 42 (i.e., result path 112), then the routine will proceed to the remote-communication portion of the process where an Internet connection is opened (S196, FIG. 5D) without establishing a data-communication connection between the DTA 42 and the field generator 40. On the other hand, if enough memory is, in fact, available in the DTA 42 to receive and store a complete set of TTFields therapy-related data from the field generator 40 (i.e., result path 114), the serial data transceiver 64 in the DTA 42 will be turned on (S116).

Figure 5A:
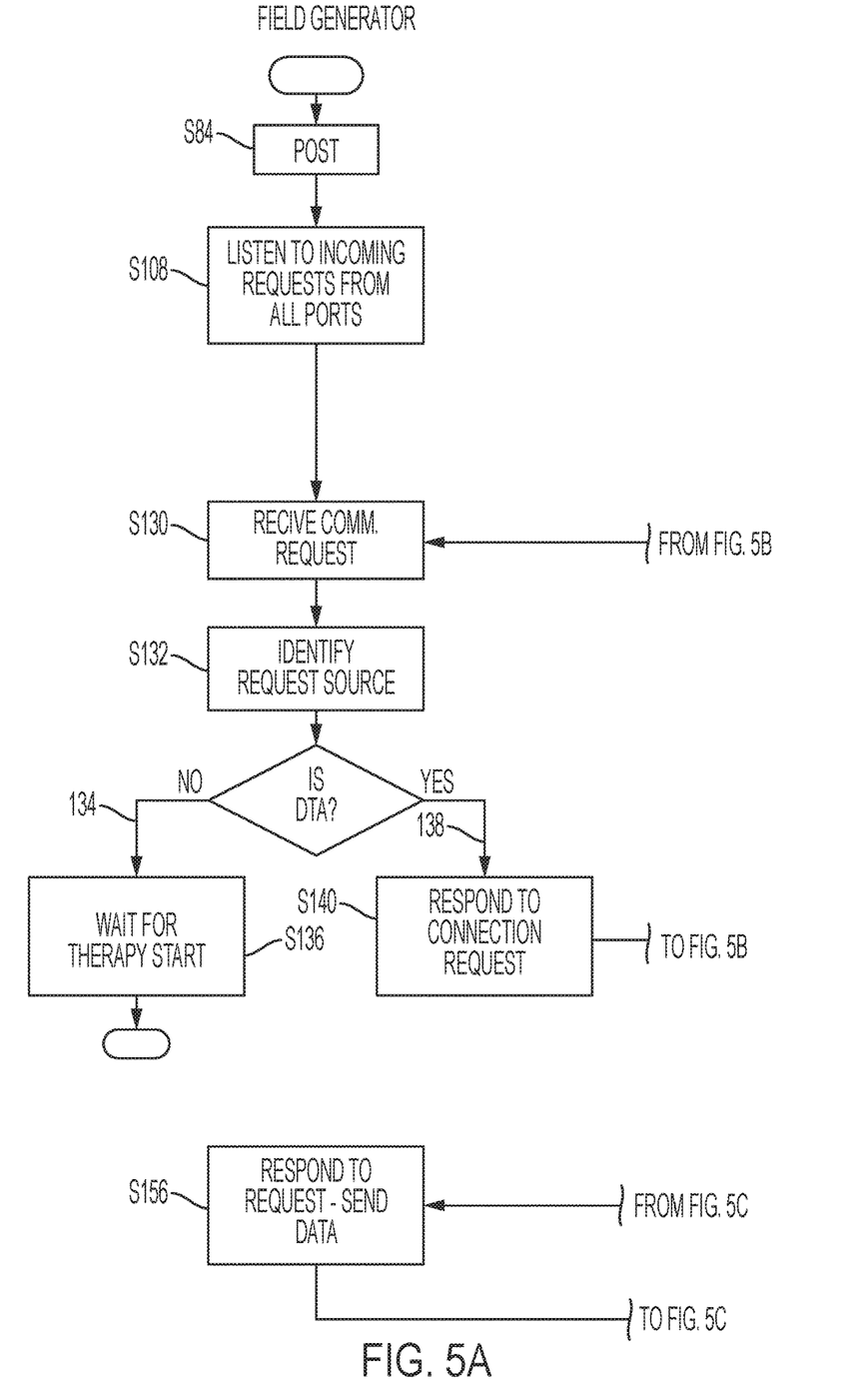
FIGS. 5A-5E present a flowchart illustrating exemplary operational logic of the DTA and the field generator illustrated in FIGS. 2A and 2B.
Figure 5B:
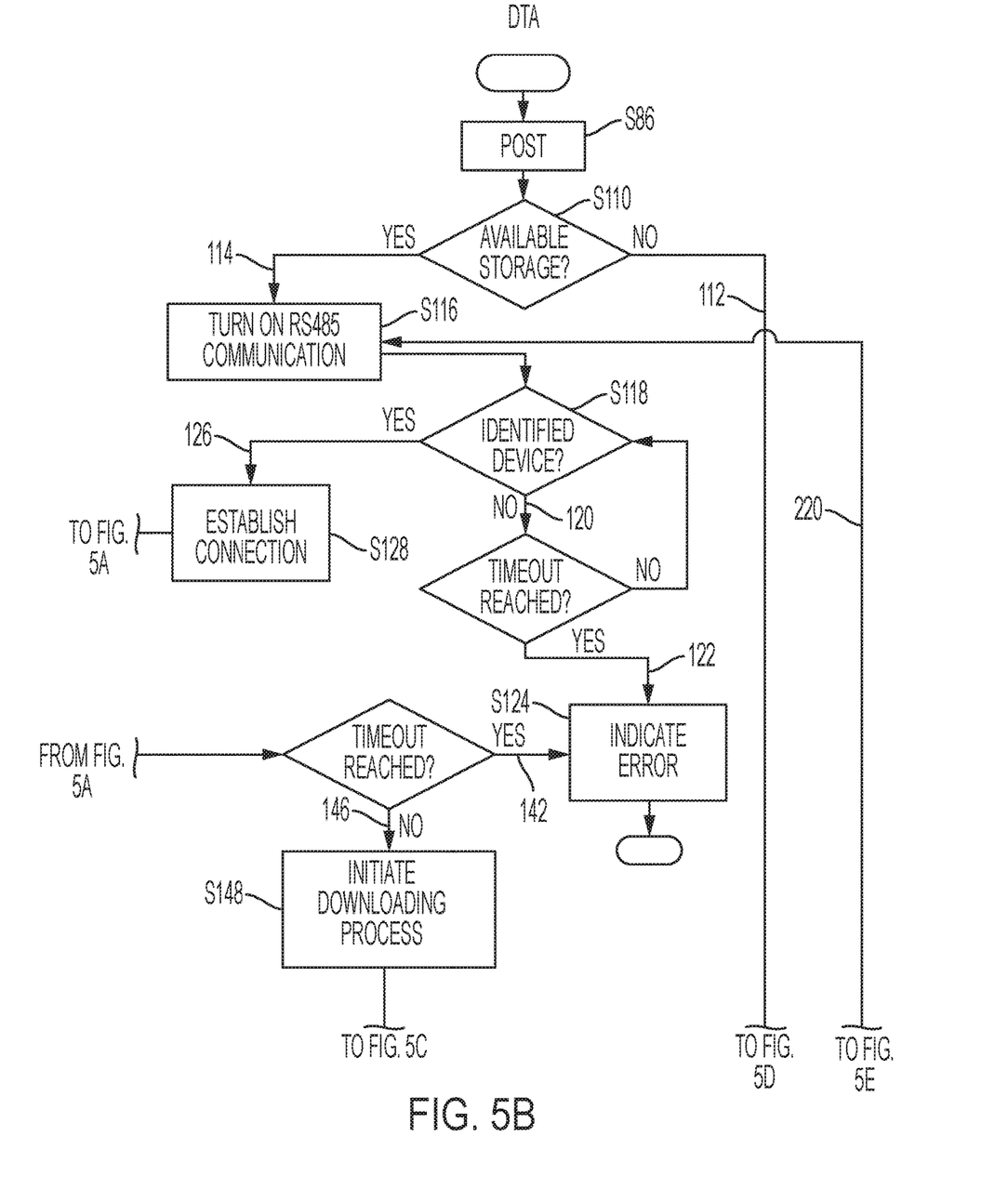

At this point in the process, the DTA 42 will start to evaluate whether another device is connected to the DTA 42 and, if so, whether the other device is recognized to be the field generator 40 (S118). One suitable approach for making this evaluation is for the DTA 42 to use (a) a switch that actuates upon physical connection of another device to the DTA 42, and (b) a sensor configured to detect that the field generator is powered on. Once the switch and sensor indicate that the field generator 40 has been connected to the DTA 42, the DTA 42 will begin listening for connection requests from the field generator 40.

If a connected device is not recognized to be the field generator 40 (result path 120), the DTA 42 will continue to try to identify the connected device until a predetermined timeout period is reached. If the timeout period is reached (i.e., result path 122), an error message is displayed (S124) and the process terminates. On the other hand, if a connected device is determined to be the field generator 40 (result path 126), then the DTA 42 attempts to establish a data-transmitting connection (S128) between it and the field generator 40—i.e., between the serial data transceiver 64 in the DTA 42 and the serial data transceiver 48 in the field generator 40—by sending a connection request to the field generator 40.

When the field generator 40 receives a connection request from another device (S130), the field generator 40 will determine (S132), e.g., from received data, which device is connected. If the connected device is a set of transducer arrays (result path 134), connected to the field generator 40 by the transducer interface 20, then the field generator 40 will wait for TTFields therapy to be initiated (S136). Once the patient initiates TTFields therapy (not indicated in FIG. 5A), e.g., by pressing a start button on the field generator 40, the field generator 40 outputs AC voltage to the transducer arrays 10 to provide TTFields therapy, as described above in connection with FIG. 2A. On the other hand, if a DTA 42 is connected (result path 138), the field generator 40 will respond to the connection request (S140) by attempting to connect to the DTA 42 to complete the data-transferring connection.

The field generator 40 will continue trying to connect to the DTA 42 until a predetermined timeout period, started when the DTA 42 sends the connection request (S128), is reached. If the timeout period is reached (i.e., result path 142), an error message is displayed (S124) and the process terminates.

On the other hand, if the field generator 40 successfully completes the data-transferring connection before the timeout period expires (result path 146), the DTA 42 will initiate the transfer of TTFields therapy-related data (S148) from the field generator 40—i.e., from memory 50—to its own memory, i.e., to EEPROM 66. To do so, the DTA 42 sends a query to the field generator 40 to determine whether any TTFields therapy-related data that has not been transmitted to the DTA 42 remains within memory 50 (S150). If non-transmitted TTFields therapy-related data is present within memory 50 (result path 152), the DTA 42 sends a request to the field generator 40 for the field generator 40 to send TTFields therapy related data to the DTA 42 (S154), and the field generator 40 responds by transmitting TTFields therapy-related data to the DTA 42 (S156).

Figure 5C:
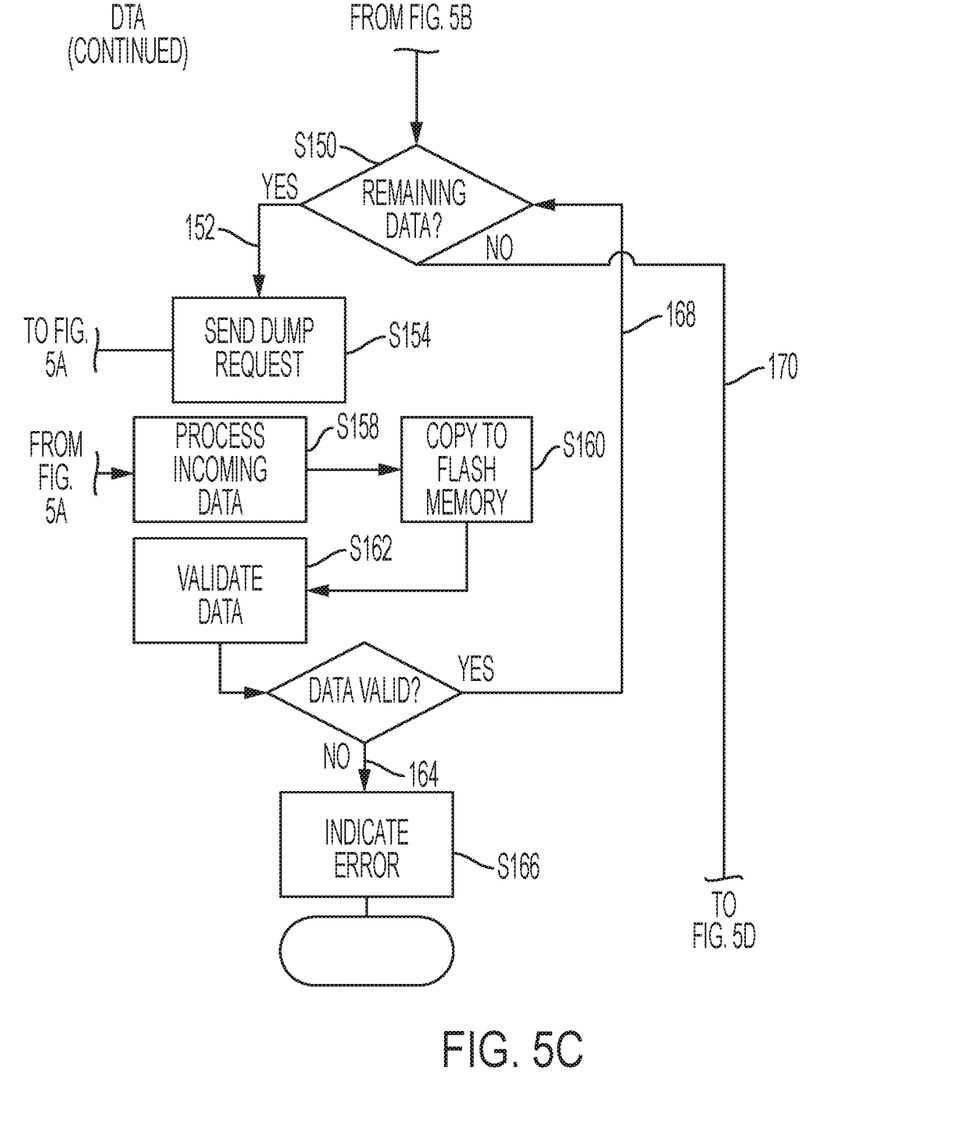

The DTA 42 processes the incoming TTFields therapy-related data (S158), copies it to EEPROM 66 (S160), and then validates the data (S162). If the data is not valid (result path 164), an error is indicated (S166) and the process terminates. Otherwise, if the data is valid (result path 168), the process returns to check once more whether any non-transmitted TTFields therapy-related data remains within memory 50 (S150).

Once there is no more non-transmitted TTFields therapy-related data remaining within memory 50 (result path 170, FIGS. 5C to 5D), the DTA will store the data in EEPROM 66 (S172). Additionally, if a flash memory reader/writer 68 is present, the validated TTFields therapy-related data will be stored in removable media present in the reader/writer 68 (S174).

Figure 5D:
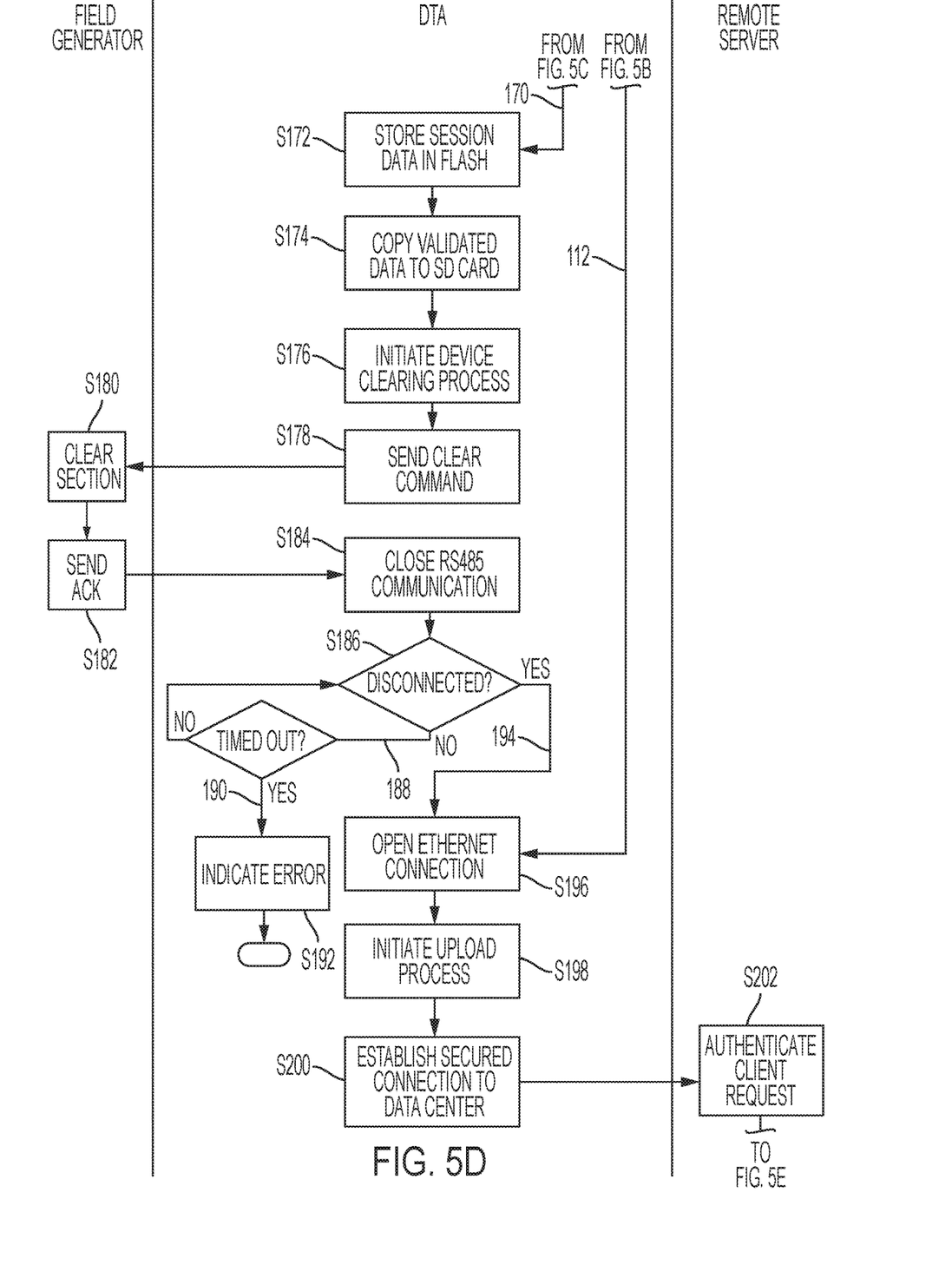

Next, the DTA 42 initiates the data-clearing process (S176) and sends a command to the field generator 40 (S178) instructing the field generator 40 to clear its memory 50 of TTFields therapy-related data. In response to this command, the field generator 40 clears its memory 50 of TTFields therapy-related data (S180) and, upon completion of the clearing step, sends an acknowledgment message back to the DTA 42 (S182) indicating that it (the field generator 40) has done so.

Upon receipt of the acknowledgement message, the DTA 42 turns off its serial data transceiver 64 (S184) to close communication with the field generator 40. The DTA 42 then checks (S186) to determine whether the field generator 40 has been disconnected from the DTA (e.g., using the switch that actuates upon physical connection of another device to the DTA). The DTA 42 will continue checking whether the field generator 40 has been disconnected from the DTA 42 so long as the field generator 40 remains connected to the DTA 42 (result path 188) and until a timeout period— initiated when the DTA 42 receives the data-cleared acknowledgment message and turns off its serial data transceiver 64—expires.

If the timeout period expires (result path 190), the DTA indicates an error (S192), e.g., by lighting an LED or displaying a message instructing the patient to disconnect the field generator 40 from the DTA 42, and all terminate processing without transmitting any data that has been previously accepted. On the other hand, once the field generator 40 has been disconnected from the DTA 42 (result path 194) the DTA will begin to transmit the TTFields therapy-related data that it has received from the field generator 40 to a remote data center server. It should be noted that the DTA 42 will never initiate a communication session with the server while the DTA remains connected to the field generator 40.

After the DTA 42 has been disconnected from the field generator 40, the DTA 42 will open a communication connection (S196) for either the onboard Internet modem 70 or cellular data modem 72, depending on which type of modem the DTA 42 has. (If the DTA 42 has both an Internet modem and a cellular data modem, the DTA 42 could be configured to allow the patient to select which mode of data communication is utilized.) The data-upload process is then begun (S198) by sending a connection request (S200) to a server at the data center.

Upon receipt of the connection request, the server will attempt to authenticate it (S202). If the connection request is not authenticated (result path 204), the connection will be refused (S206) and an error message will be displayed on the DTA 42. On the other hand, if the connection request is authenticated (result path 208), the remote server will send a message to the DTA 42 (S210) accepting the connection request.

Once the DTA 42 receives the message indicating that the connection request has been accepted, it checks (S212) whether any TTFields therapy-related data is in its memory 66 that has not yet been uploaded to the data center. If there is no remaining data to be uploaded (result path 214), the communications connection is closed (S216), and the TTFields therapy-related data stored in the DTA's memory 66 is cleared (S218). The process then returns (path 220, FIG. 5E back to FIG. 5B) to the DTA's serial data transceiver 64 being turned back on (S116), at which point the DTA 42 begins again to check for a device being connected to it. On the other hand, if there is, in fact, data in the DTA's memory 66 remaining to be uploaded (result path 224), the DTA 42 will transmit a data packet (S226) to the remote server.

Figure 5E:
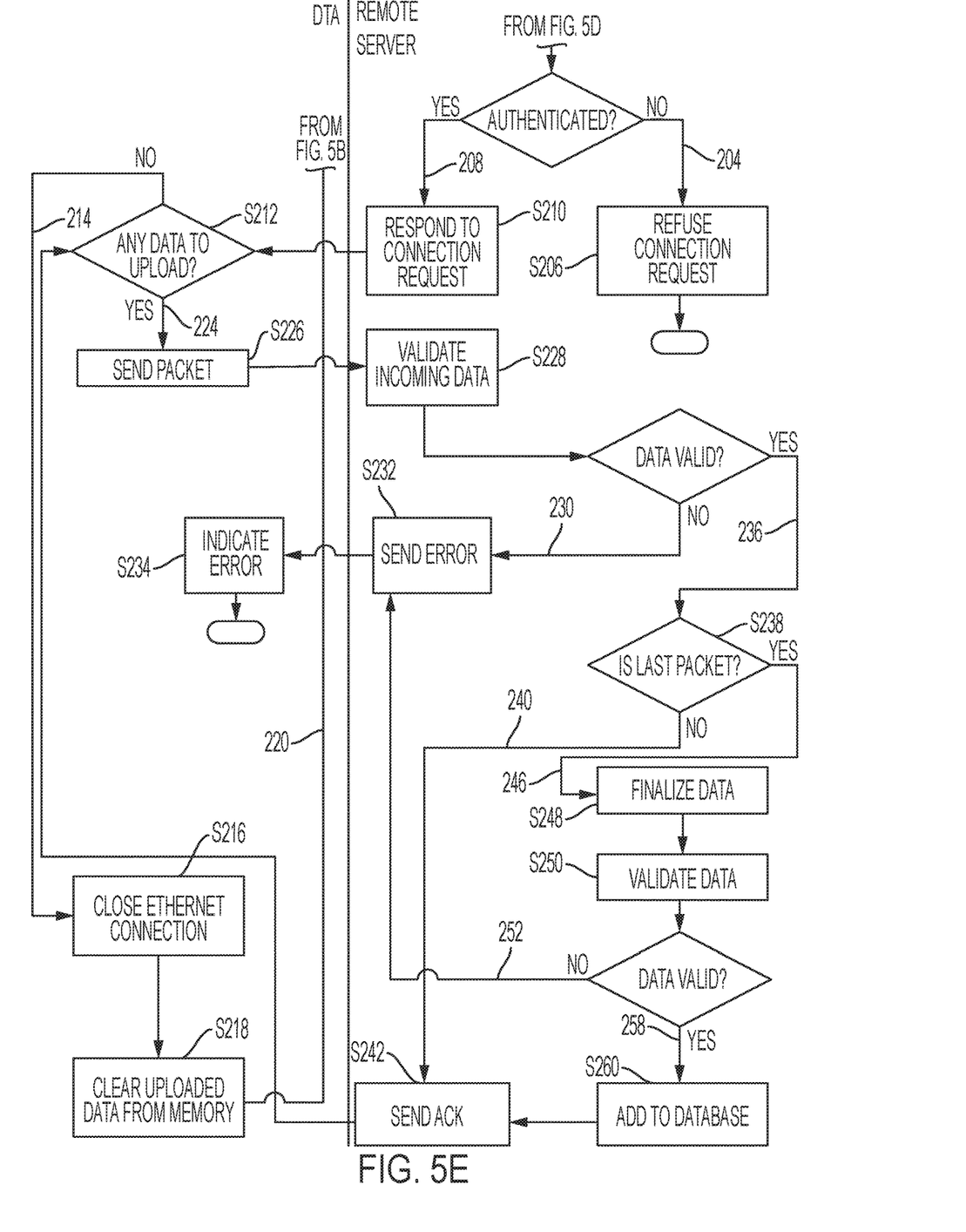

Upon receipt of the data packet, the remote server validates the incoming data packet (S228). If the incoming data packet is not valid (result path 230), the remote server sends an error message to the DTA 42 (S232), and the DTA displays a communications error indicator (S234). On the other hand, if the incoming data packet is, in fact, valid (result path 236), the remote server examines the packet (S238) to see whether it is the last packet in the transmission of a given unit of data. If the received packet is not the last packet (result path 240), the remote server will send a message to the DTA 42 (S242) acknowledging receipt of the data packet, and the DTA 42 will again check to see (S212) whether any non-transmitted data remains in its memory 66. So long as unsent data remains (result path 224), the DTA 42 will continue to send data packets to the remote server.

When a received packet is the last packet in the transmission of a given unit of data (result path 246), the remote server finalizes the data (S248) by assembling the packets, and it then attempts to validate the assembled data (S250). If the assembled data is not valid (result path 252), the remote server will send an error message to the DTA 42 (S232), and the DTA 42 will display a communication error indicator (S234). On the other hand, if the assembled data is, in fact, valid (result path 258), it will be added to a database on the remote server (S260). The remote server then sends a message to the DTA 42 (S242) acknowledging receipt of the data packet, and the DTA 42 will once again check to see (S212) whether any non-transmitted data remains in its memory 66.

This process will repeat until there is no more non-transmitted data remaining in the memory 66 of the DTA 42 (result path 214). When this point is reached, the data-transmitting connection to the remote server is closed (S216) and TTFields therapy-related data is cleared (S218) from the memory 66 of the DTA 42. The process then returns (path 220, FIG. 5E back to FIG. 5B) to the DTA's serial data transceiver 64 being turned on and the DTA 42 checking for a device being connected to it.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A TTFields (tumor-treating fields) therapy field generator comprising:
   an AC voltage generator;
   a serial data transceiver;
   a memory;
   a single first connector having 1) a first plurality of pins for outputting an AC voltage generated by the AC voltage generator, and 2) a second plurality of pins for conveying serial data to and from the serial data transceiver; and
   a controller programmed to execute instructions that cause the field generator to perform the following steps:
   (1) determining if a transducer interface has been connected to the first connector,
   (2) after determining that the transducer interface has been connected to the first connector, activating the AC voltage generator so that an AC voltage appears across the first plurality of pins of the first connector, and storing data relating to TTFields treatment in the memory,
   (3) determining if a data transfer apparatus has been connected to the first connector, and
   (4) after determining that a data transfer apparatus has been connected to the first connector, retrieving the data related to TTFields treatment from the memory and routing the retrieved data to the serial data transceiver so that the serial data transceiver outputs the data relating to TTFields treatment via the second plurality of pins of the single first connector.

2. The field generator according to claim 1, wherein the controller is programmed to determine that a transducer interface has been connected to the first connector by examining data received via the serial data transceiver.

3. The field generator according to claim 1, wherein the controller is programmed to determine that a data transfer apparatus has been connected to the first connector by examining data received via the serial data transceiver.

4. The field generator according to claim 1, wherein the controller is programmed to clear data relating to TTFields treatment from the memory after the data relating to TTFields treatment has been output by the serial data transceiver.

5. The field generator according to claim 1, wherein the data relating to TTFields therapy stored in the memory includes one or more of time and date of treatment sessions, current applied by each transducer array in a set of transducer arrays that has been connected to the first connector, measured temperature values, and operational anomalies.

6. A TTFields (tumor-treating fields) therapy system with enhanced diagnostics, the system comprising:
   a field generator; and
   a data transfer apparatus,
   wherein the field generator includes
      an AC voltage generator,
      a first serial data transceiver,
      a first memory,
      a single first connector having 1) a first plurality of pins for outputting an AC voltage generated by the AC voltage generator, and 2) a second plurality of pins for conveying serial data to and from the first serial data transceiver, and
      a first controller programmed to execute instructions that cause the field generator to perform the following steps:
         (1) determining if a transducer interface has been connected to the first connector,
         (2) after determining that the transducer interface has been connected to the first connector, activating the AC voltage generator so that an AC voltage appears across the first plurality of pins of the first connector, and storing data relating to TTFields treatment in the first memory,
         (3) determining if a data transfer apparatus has been connected to the first connector, and
         (4) after determining that a data transfer apparatus has been connected to the first connector, retrieving the data related to TTFields treatment from the first memory and routing the retrieved data to the first serial data transceiver so that the first serial data transceiver outputs the data relating to TTFields treatment via the second plurality of pins of the single first connector, and
   wherein the data transfer apparatus includes
      a second serial data transceiver,
      a second memory,
      a modem,
      a second connector configured to interface with the first connector, and a second controller programmed to execute instructions that cause the data transfer apparatus to execute the following steps:
         (1) determining that the field generator has been connected to the data transfer apparatus,
         (2) after determining that the field generator has been connected to the data transfer apparatus, causing the second serial data transceiver to accept serial data from the field generator and to store the accepted data in the second memory, wherein the accepted data is data relating to treatment of a patient using TTFields, (3) after accepting the data from the field generator, determining whether the field generator has been disconnected from the data transfer apparatus, and (4) after determining that the field generator has been disconnected from the data transfer apparatus, retrieving data relating to treatment of a patient using TTFields from the second memory and causing the modem to transmit the retrieved data to a remote server.

7. The system according to claim 6, wherein the first controller is programmed to (a) determine that the transducer interface has been connected to the first connector by examining data received via the first serial data transceiver, and (b) determine that the data transfer apparatus has been connected to the first connector by examining data received via the first serial data transceiver.

8. The system according to claim 6, wherein the first controller is programmed to clear data relating to TTFields treatment from the first memory after the data relating to TTFields treatment has been output by the first serial data transceiver.

9. The system according to claim 6, wherein the data relating to TTFields therapy stored in the first memory includes one or more of time and date of treatment sessions, current applied by each transducer array in a set of transducer arrays that has been connected to the first connector, measured temperature values, and operational anomalies.

10. The system of claim 6, wherein the connection between the field generator and the data transfer apparatus interface is implemented by mating the second connector directly to the first connector.

11. The system of claim 6, wherein the connection between the field generator and the data transfer apparatus interface is implemented by connecting a cable between the second connector and the first connector.

* * * * *